(12) United States Patent
Sasaki et al.

(10) Patent No.: US 9,851,331 B2
(45) Date of Patent: Dec. 26, 2017

(54) STRUCTURE ANALYZING DEVICE AND A STRUCTURE ANALYZING METHOD

(71) Applicant: NEC CORPORATION, Tokyo (JP)

(72) Inventors: Yasuhiro Sasaki, Tokyo (JP);
Masatake Takahashi, Tokyo (JP);
Shigeki Shinoda, Tokyo (JP)

(73) Assignee: NEC CORPORATION, Tokyo (JP)

( * ) Notice: Subject to any disclaimer, the term of this patent is extended or adjusted under 35 U.S.C. 154(b) by 131 days.

(21) Appl. No.: 14/406,242

(22) PCT Filed: Jan. 11, 2013

(86) PCT No.: PCT/JP2013/050415
§ 371 (c)(1),
(2) Date: Dec. 8, 2014

(87) PCT Pub. No.: WO2013/183313
PCT Pub. Date: Dec. 12, 2013

(65) Prior Publication Data
US 2015/0177195 A1    Jun. 25, 2015

(30) Foreign Application Priority Data
Jun. 6, 2012  (JP) ................................ 2012-129199

(51) Int. Cl.
*G01N 29/12*    (2006.01)
*G01N 29/04*    (2006.01)
(Continued)

(52) U.S. Cl.
CPC ............ *G01N 29/12* (2013.01); *G01M 3/243* (2013.01); *G01M 7/00* (2013.01); *G01N 29/045* (2013.01);
(Continued)

(58) Field of Classification Search
CPC ........ G01N 29/12; G01N 29/11; G01N 29/14; G01N 29/42; G01N 29/045;
(Continued)

(56) References Cited

U.S. PATENT DOCUMENTS 3,023,609 A * 3/1962 Schubring .............. G01N 29/04
73/579
4,901,575 A * 2/1990 Bohannan ................ G01H 1/00
73/587

(Continued)

FOREIGN PATENT DOCUMENTS

JP         03-120458      5/1991
JP         05-180809      7/1993
(Continued)

OTHER PUBLICATIONS

Machine Translation of JP 5-180809.*
(Continued)

*Primary Examiner* — Laura Martin
*Assistant Examiner* — Rose M Miller
(74) *Attorney, Agent, or Firm* — Young & Thompson

(57) ABSTRACT

Disclosed is a structure analyzing device and a structure analyzing method which can analyze a state change of a structure, which is caused before the structure is destroyed, such as a state change of degradation of the structure or the like. A structure analyzing device (10) includes a vibration detecting unit (11) which detects a vibration of a structure, and an analysis unit (12) which analyzes an output signal of the vibration detecting unit (11). The analysis unit (12) analyzes a state change of the structure by comparing a value of resonant sharpness Q, which is measured by use of the following formula (1) in a state existing when carrying out
(Continued)

analysis, with a value of resonant sharpness Q which is measured by use of the following formula (1) in a standard state.

15 Claims, 7 Drawing Sheets

(51) Int. Cl.
*G01N 29/44* (2006.01)
*G01M 3/24* (2006.01)
*G01M 7/00* (2006.01)

(52) U.S. Cl.
CPC . *G01N 29/4436* (2013.01); *G01N 2291/0258* (2013.01)

(58) Field of Classification Search
CPC ......... G01N 29/4436; G01N 2291/014; G01N 2291/0258; G01M 3/243; G01M 7/00; G01M 7/08
USPC .................. 73/579, 582, 586, 587, 588, 592
See application file for complete search history.

(56) References Cited

U.S. PATENT DOCUMENTS

| | | | |
|---|---|---|---|
| 5,144,838 A | 9/1992 | Tsuboi | |
| 5,257,544 A * | 11/1993 | Khuri-Yakub | G01H 13/00 73/579 |
| 7,798,000 B1 * | 9/2010 | Murray | G01B 17/02 73/579 |
| 2004/0123665 A1 * | 7/2004 | Blodgett | G01H 3/00 73/579 |
| 2010/0307248 A1 * | 12/2010 | Hayashi | G01N 29/14 73/579 |
| 2010/0324839 A1 * | 12/2010 | Martin | G01M 3/243 702/56 |
| 2013/0213137 A1 * | 8/2013 | Ostapenko | G01N 29/12 73/582 |

FOREIGN PATENT DOCUMENTS

| | | |
|---|---|---|
| JP | 10-221197 | 8/1998 |
| JP | 11-14492 | 1/1999 |
| JP | 2001-349775 | 12/2001 |
| JP | 2008-008707 | 1/2008 |
| JP | 2011-027452 | 2/2011 |

OTHER PUBLICATIONS

International Search Report PCT/JP2013/050415 dated Apr. 9, 2013.

Hitoshi Domon et al.—Easy Non-Destructive Testing Techniques—Inspecting material/machines/buildings without destroying them—K Books Series 113—Jan. 1996—pp. 1-9.

* cited by examiner

STRUCTURE ANALYZING DEVICE AND A STRUCTURE ANALYZING METHOD

TECHNICAL FIELD

The present invention relates to a structure analyzing device and a structure analyzing method.

BACKGROUND ART

In order to ensure safety and secure for a structure such as a high-pressure pipe line, a water and sewage plumbing, a high speed railway, a long span bridge, a high rise building, a large passenger aircraft or a car, non-destructive inspection techniques have been researched and developed. As the non-destructive inspection of the structure, the crack detecting method by penetration inspection and the crack detecting method by ultrasonic inspection are exemplified (for example, refer to a non-patent literature 1). FIG. 9A shows an outline of the crack detecting method by penetration inspection. The crack detecting method by penetration inspection is a method to apply a fluorescent material 2 to a member 1 which is a component of a facility, and to make the fluorescent material 2, which penetrates into a crack 3 corresponding to a defect of the structure, luminous, and to check the crack 3 by inspector's eyes. Since a check based on the method can be carried out with ease, the method is used frequently. FIG. 9B shows an outline of the crack detecting method by ultrasonic inspection. The crack detecting method by ultrasonic inspection is a method to use an ultrasonic transducer 4 which is an electromechanical converter, and to identify a crack 3 of a member 1 by radiating ultrasonic waves to the member 1. The method uses a property that acoustic impedance at a location, at which the crack 3 is caused, is different from acoustic impedance at a normal location. Identification of the crack 3 of the member 1 is carried out through receiving a reflected wave, which is generated by reflection of an ultrasonic wave signal propagating through the member 1 and which is generated at the location of the crack 3, by use of the electromechanical converter.

CITATION LIST

Non Patent Literature

NPL 1: Easy non-destructive inspection technique, fifth page, 1996, Kogyo Chosakai Publishing Co., Ltd.

SUMMARY OF INVENTION

Technical Problem

Since each of the crack detecting method by penetration inspection and the crack detecting method by ultrasonic inspection detects the defect of the structure such as the crack after the defect of the structure is caused, it is difficult to detect a degradation state before the defect is caused. However, once the defect is caused, even if the defect is slight, there is a fear that the defect may bring about a serious result. Therefore, it is requested to realize an inspection method which can detect the degradation state before the defect is caused.

An object of the present invention is to provide a structure analyzing device and a structure analyzing method which can analyze a state change of the structure, for example, a state change of degradation of the structure or the like which is caused before the structure is destroyed.

Solution to Problem

In order to achieve the above-mentioned object, a structure analyzing device of the present invention includes:
a vibration detecting means which detects a vibration of a structure; and
an analysis means which analyzes an output signal of the vibration detecting means.

The analysis means is a means which analyzes a state change of the structure by comparing a value of resonant sharpness Q, which is measured by use of the following formula (1) in a state existing when carrying out the analysis, with a value of resonant sharpness Q which is measured in a standard state.

$$Q = f/\Delta f \quad (1)$$

where f is a resonant frequency of the structure, and $\Delta f$ is a full width at half maximum.

A structure analyzing method of the present invention includes:
a vibration detecting step in which a vibration of a structure is detected; and
an analysis step in which an output signal in the vibration detecting step is analyzed.

The analysis step is a step in which a state change of the structure is analyzed by comparing a value of resonant sharpness Q, which is measured by use of the following formula (1) in a state existing when carrying out the analysis, with a value of resonant sharpness Q which is measured in a standard state.

$$Q = f/\Delta f \quad (1)$$

where f is a resonant frequency of the structure, and $\Delta f$ is a full width at half maximum.

Advantageous Effects of Invention

According to the structure analyzing device and the structure analyzing method of the present invention, it is possible to analyze the state change of the structure, for example, the state change of the degradation of the structure or the like which is caused before the structure is destroyed.

DESCRIPTION OF EMBODIMENTS

Hereinafter, examples of a structure analyzing device and a structure analyzing method of the present invention will be described in detail with reference to drawings. However, the present invention is not limited to examples which will be described later. Here, in FIGS. 1 to 8 shown in the following, the same code is attached to the same part. Moreover, in each diagram, composition of each unit may be simplified appropriately for convenience of explanation in some cases, and a size ratio or the like of each unit may be indicated schematically, and as a result may be different from an actual size ratio or the like.

Exemplary Embodiment 1

Figure 1:
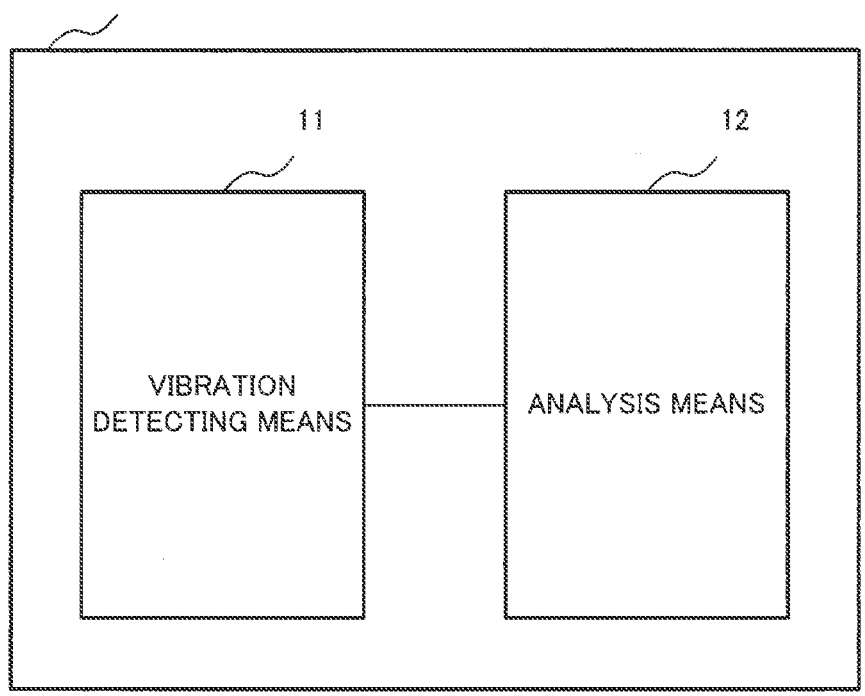
FIG. 1 is a block diagram showing composition of an example of a structure analyzing device (exemplary embodiment 1) of the present invention.

FIG. 1 is a block diagram showing composition of a structure analyzing device of an exemplary embodiment 1.

Figure 2:
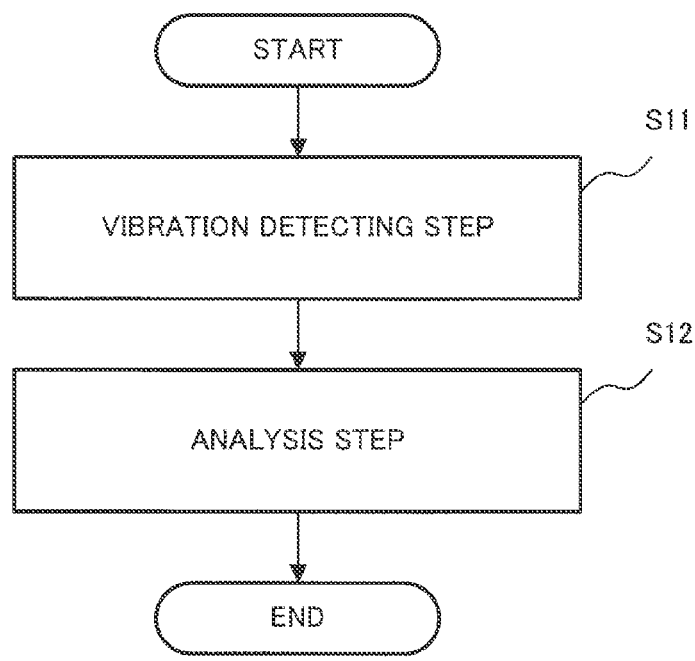
FIG. 2 is a flowchart showing an example of a structure analyzing method (exemplary embodiment 1) of the present invention.

FIG. 2 is a flowchart of a structure analyzing method in the exemplary embodiment 1.

As shown in FIG. 1, a structure analyzing device 10 of the exemplary embodiment includes a vibration detecting means 11 and an analysis means 12 as a main component.

The vibration detecting means 11, which is, for example, a vibration sensor, detects vibration of a structure, and acquires vibration waveform data from the structure. A kind of the vibration sensor is not limited in particular, and the well-known vibration sensor can be applied. Specifically, an acceleration sensor, a velocity sensor and a displacement sensor are exemplified. It is preferable that the acceleration sensor is a piezoelectric type and includes a signal amplifier circuit. It is preferable that the vibration detecting means 11 (vibration sensor) has high sensitivity, and can detect a signal which has a wide frequency bandwidth. A contact type vibration detecting means, which is arranged on the structure, is applicable to the vibration detecting means 11. An arrangement position on the structure is not limited in particular. The vibration detecting means 11 is arranged at an appropriate position on the structure on the basis of a purpose of using the structure analyzing device 10. Moreover, it is also possible to apply a non-contact type vibration detecting means, which can be arranged apart from the structure, to the vibration detecting means 11. For example, by applying a laser Doppler vibrometer or the like to the vibration detecting means 11, a frequency response of a vibration amplitude may be measured optically. It is possible to obtain the same result as a result which is obtained with a plurality of vibration sensors being arranged to measure the frequency response as mentioned later when the frequency response of the vibration amplitude is measured with the laser Doppler vibrometer being moved on a surface of the structure in order to scan the surface. Since it is possible to arrange the non-contact type vibration detecting means without coming into contact with the structure which is an analysis target, it is effective to use the non-contact type vibration detecting means in the case that it is impossible to arrange the vibration detecting means on the structure, for example, in the case of a severely uneven area, a hot or cold area, an area on a small member or the like. Moreover, the non-contact type vibration detecting means can be employed even in the case that its weight might cause an influence to the attachment, when being attached to the analysis target structure which is, for example light or soft. Moreover, in the case that an antenna is arranged in place of the vibration sensor to emit an electromagnetic wave, it is possible to measure the frequency response of the vibration amplitude on the basis of a voltage output response of a reflected wave. In the case of making the antenna move on the surface of the structure in order to scan the surface, and measuring the frequency response of the vibration amplitude, it is possible to obtain the same result as a result which is obtained in the case that a plurality of vibration sensors are arranged to measure the frequency response as mentioned later.

The analysis means 12, which is a means analyzing an output signal of the vibration detecting means 11, analyzes a state change of the structure by comparing a value of resonant sharpness Q, which is measured by use of the following formula (1) in a state existing when carrying out analysis, with a value of resonant sharpness Q which is measured in a standard state.

$$Q = f/\Delta f \quad (1)$$

where f is a resonant frequency of the structure, and $\Delta f$ is a full width at half maximum.

The standard state is, for example, a state measured before the state change is caused.

That is, in the case of analyzing degradation of the structure, the standard state means a normal state in which the degradation is not caused.

It is preferable that the value measured in the standard state is stored, for example, in a storage means, and the analysis means reads the value, which is measured in the standard state, from the storage means, and compares the value, which is measured in the state existing when carrying out the analysis, with the value which is measured in the standard state.

The structure analyzing method of the exemplary embodiment carries out the following steps, which are shown in FIG. 2, with using the structure analyzing device shown in FIG. 1.

First, the vibration detecting means 11 detects the vibration of the structure which is a detection target, and acquires the vibration waveform data (vibration detecting step (Step S11))

Next, the analysis means 12 analyzes the output signal of the vibration detecting means 11 which is the vibration waveform data acquired from the vibration detecting means 11 (analysis step (Step S12)). The analysis step (Step S12) is a step to analyze the state change of the structure by comparing the value of the resonant sharpness Q, which is measured by use of the above-mentioned formula (1) in the state of analysis, with the value of the resonant sharpness Q which is measured in the standard state.

A feature of the present invention is to detect the state change (for example, mechanical distortion of the structure) due to the vibration by use of the arranged vibration detecting means, and to measure the resonant frequency and the resonant sharpness Q, which are determined by a size and stiffness of the structure, on the basis of the frequency response of the vibration amplitude. A relation among a resonant frequency f, stiffness E and mass M of a member is represented in a formula $f^2 \propto E/M$. Moreover, a relation among the resonant sharpness Q, a mechanical resistance R and the mass M of the member is expressed in a formula of $Q \propto M/R$. For example, when force is applied to the structure from the outside, mechanical distortion is caused to the structure, and an atom which is included in the structure is moved, and afterward coupling among the atoms is disconnected and consequently the structure results in being damaged (being caused defects). When an atom is moved, mechanical characteristics, especially, the stiffness and the mechanical resistance change. According to the present invention, by measuring the resonant sharpness Q it is possible to carry out a quantitative evaluation with high level accuracy of these changes as the state of degradation of the sign of structural damage are caused.

Figure 3:
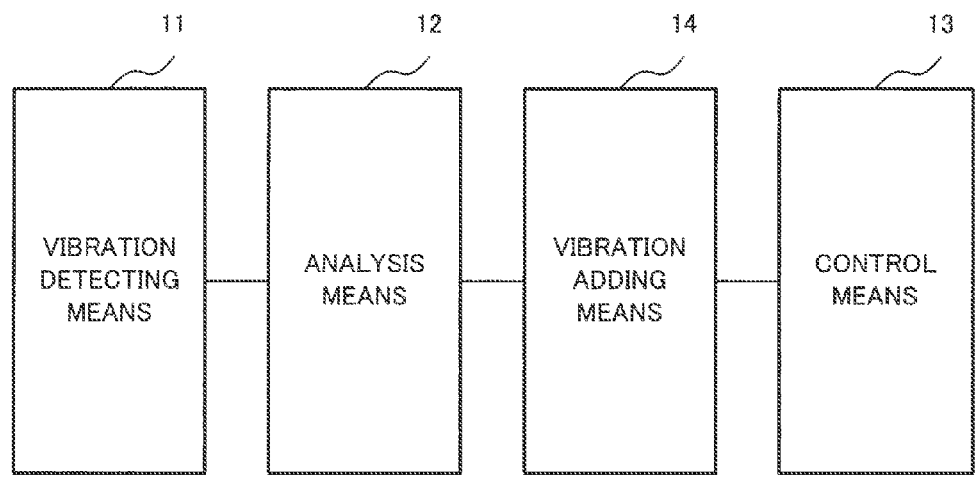
FIG. 3 is a block diagram showing composition of a modification 1 of the structure analyzing device of the exemplary embodiment 1.
Figure 4:
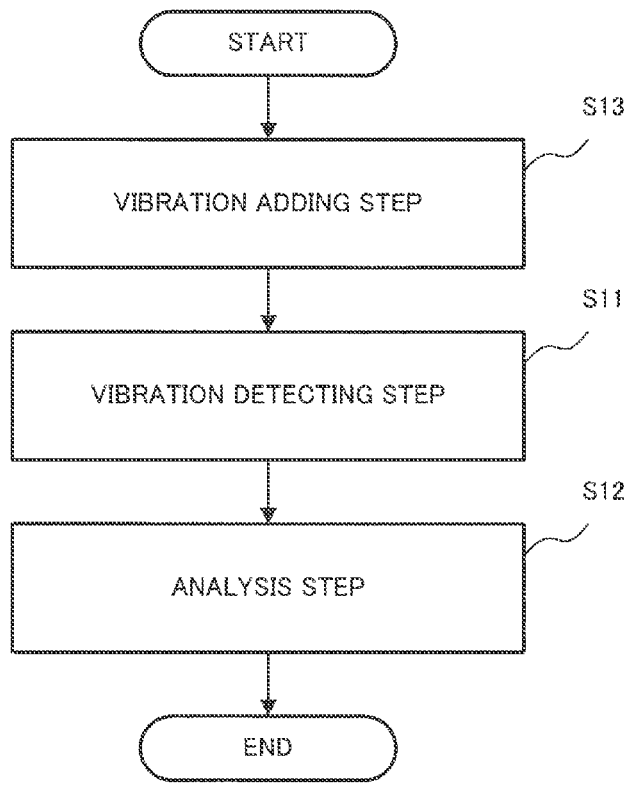
FIG. 4 is a flowchart showing a modification 1 of the structure analyzing method of the exemplary embodiment 1.

It is also preferable that the vibration, which is detected by the vibration detecting means 11, is added to the structure by a vibration adding means which vibrates the structure, and it is preferable that the structure analyzing device of the exemplary embodiment includes the vibration adding means furthermore. FIG. 3 is a block diagram showing composition of a structure analyzing device, which including the vibration adding means, according to a modification 1 of the exemplary embodiment 1. Moreover, FIG. 4 is a flowchart showing a structure analyzing method in the modification 1. As shown in FIG. 3, the analyzing device of the modification 1 includes a vibration adding means 13 and a control means 14 in addition to the vibration detecting means 11 and the analysis means 12. The control means 14, which is a means to control the vibration detecting means 11, the analysis means 12 and the vibration adding means 13, includes, for example, a constant voltage oscillation circuit or the like, and applies a vibration waveform to the vibration adding means 13 to vibrate the vibration adding means 13.

Moreover, since the control means 14 is an optional component, and may not be included in the structure analyzing device, but it is preferable that the control means is included. Except for this point, the structure analyzing device shown in FIG. 3 has the same composition as the structure analyzing device 10 shown in FIG. 1 has. The structure analyzing method of the modification 1 includes a vibration adding step (S13) before the vibration detecting step (S11). Except for this point, the structure analyzing method shown in FIG. 4 includes the same step as the structure analyzing method shown in FIG. 2 includes.

It is enough if the vibration adding means 13 can add the vibration to the structure of the analysis target. For example, a vibration adder, a speaker or the like is applicable to the vibration adding means 13, and can be selected appropriately according to a measurement environment or the like. The vibration adder receives an alternating voltage waveform of predetermined amplitude and frequency is swept (for example, refer to FIG. 5A), from the constant voltage oscillator for a predetermined time, and vibrates the structure of the analysis target, with vibration energy into which the applied electric energy is converted. In the case of using the speaker, the speaker emits sound waves, and vibrates the structure of the analysis target.

Figure 5A:
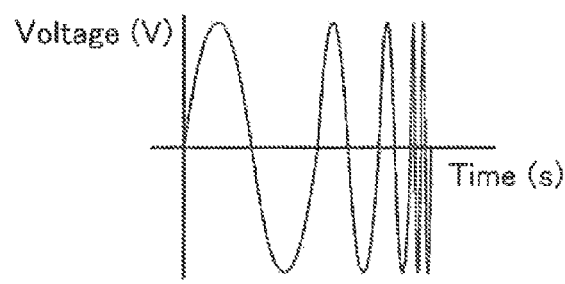
FIGS. 5A-5E are diagrams explaining the structure analyzing method in the exemplary embodiment 1 of the present invention.
Figure 5B:
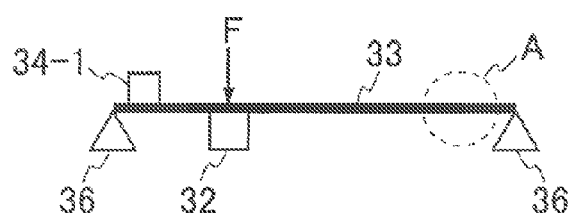
Figure 5C:
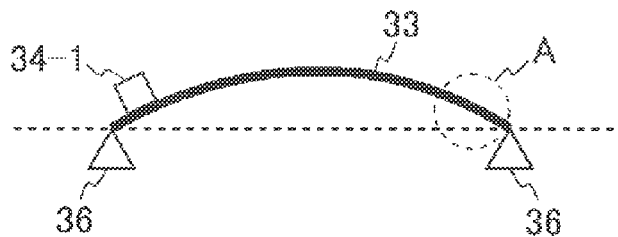
Figure 5D:
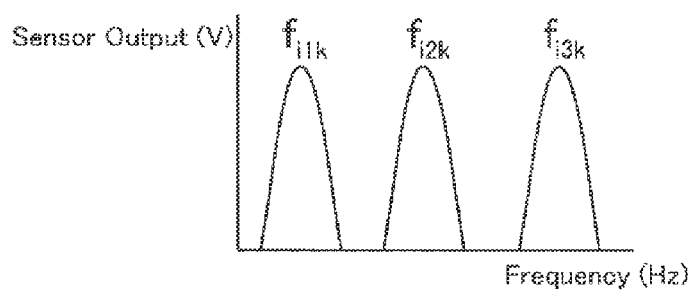

Here, a mechanism of the structure analyzing method of the present invention will be described with reference to FIG. 5. FIG. 5B is a model diagram showing a case that a measurement object 33, on which a vibration sensor 34-1 is arranged, is arranged on a pedestal 36, and is vibrated by a vibration adder 32. An A part of the measurement object 33 is caused mechanical degradation as time passes. The vibration adder 32 adds the vibration, for example, according to the following way. First, the vibration adder 32 is arranged at a position F, and adds the vibration to the measurement object 33. At this time, a resonant phenomenon whose frequency is specific and which is based on mechanical characteristics of the measurement object 33 is generated in the measurement object 33 (FIG. 5C). The vibration sensor 34-1 outputs a voltage signal according to the vibration amplitude of the measurement object 33 and generates a plurality of resonant frequency responses as shown in FIG. 5D. Here, the resonant frequency of the vibration amplitude which is measured by a vibration sensor i arranged on the measurement object, and the resonant sharpness Q are denoted as $f_{ijk}$ and $Q_{ijk}$ respectively where, i is number which identifies the arranged vibration sensor, j which is the number assigned to a resonant mode expressed as j=1, 2, 3 . . . order of lowness of frequency. Moreover, k, which indicates an order determined according to a length of time when the measurement object is used, is expressed as k=1, 2, 3 . . . in turn according to the length of time, that is, from an unused measurement object, in other word, from the measurement object which is not degraded.

Figure 5E:
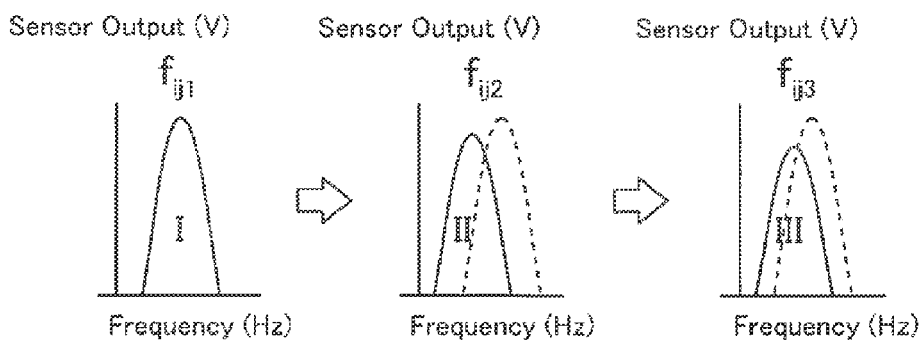

As shown in FIG. 5(e), as the time when the measurement object is used becomes long, that is, as k=1, 2, 3, . . . , the mechanical degradation is caused according to durability of a member, and consequently the resonant sharpness $Q_{ijk}$, which is calculated based on the resonant frequency $f_{ijk}$ measured by the vibration sensor 34-1, is changed. Here, it is possible to calculate the resonant sharpness $Q_{ijk}$ on the basis of the resonant frequency $f_{ijk}$ and a difference $\Delta f_{ijk}$ between frequencies, at each of which a value is half of a peak value, by use of a formula of $Q = f_{ijk}/\Delta f_{ijk}$.

It is possible to carry out a quantitative evaluation on a degree of degradation of the measurement object by use of a formula $Q_{ijk}/Q_{ijl}$.

Here, according to the method which is described in Background Art, it is impossible or difficult to detect an internal change which indicates a stage (sign) of being just before the structure is caused to the damage. On the other hand, in the case of using the resonant sharpness Q according to the present invention, it is possible to grasp such the degradation state.

Exemplary Embodiment 2

According to the exemplary embodiment, a plurality of vibration detecting means 11 are arranged. Except for this point, a structure analyzing device and a structure analyzing method of the exemplary embodiment have the same composition as the structure analyzing device and the structure analyzing method of the exemplary embodiment 1 respectively have.

Figure 6A:
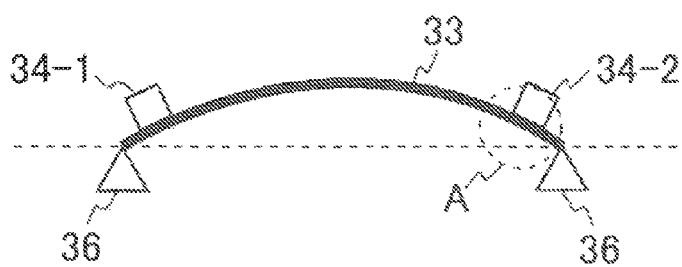
FIGS. 6A and 6B are diagrams explaining a structure analyzing method in an exemplary embodiment 2 of the present invention.
Figure 6B:
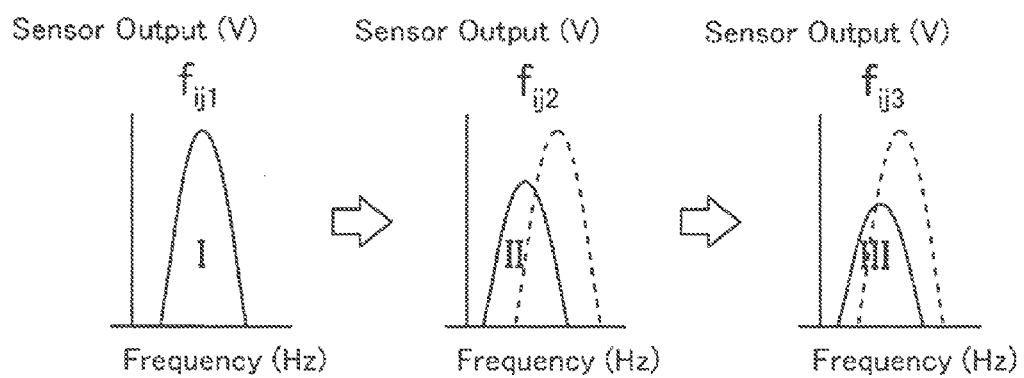

A mechanism of the structure analyzing method, which is used in the case that two vibration sensors of the vibration sensor 34-1 and a vibration sensor 34-2 are arranged on the measurement object 33 as shown in FIG. 6A, will be described. In FIG. 6A, the vibration adder is arranged at a position on the measurement object 33, and vibrates the measurement object 33. Mechanical degradation is caused at an A part of the measurement object 33 as time passes. The vibration sensor 34-2 is arranged just on the A part (degradation position). The vibration sensor 34-2 outputs a voltage signal according to vibration amplitude of the measurement object 33, and consequently generates a plurality of resonant frequency responses similarly to the exemplary embodiment 1, and an aging change as shown in FIG. 6B is caused. Here, in comparison with the change of the resonant sharpness at the vibration sensor 34-1 (FIG. 5(e)), it is found out that a change shown in FIG. 6B becomes large. In this case, since mechanical distortion becomes large at the degradation position A, the measurement value reflects the response sensitively. In the case that the vibration sensor is arranged just on the degradation position as mentioned above, the response change becomes large. As a result, it is found that it is possible to inspect (analyze) a degree of degradation with high level precision. Furthermore, it is possible to carry out analysis on identification of the degradation position or the like in comparison with largeness of a response change of a sensor which is arranged at another position.

Exemplary Embodiment 3

According to the present exemplary embodiment, the vibration adding means 13 adds a vibration, whose frequency is swept, to the structure, and then an analysis is carried out on the basis of a high order resonant frequency. Except for this point, a structure analyzing device and a structure analyzing method of the exemplary embodiment have the same composition those of the exemplary embodiment 1 or 2.

Figure 7A:
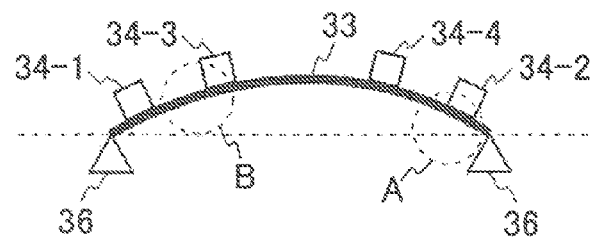
FIGS. 7A-7E are diagrams explaining a structure analyzing method in an exemplary embodiment 3 of the present invention.
Figure 7B:
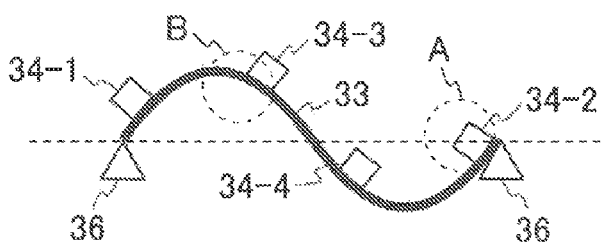
Figure 7C:
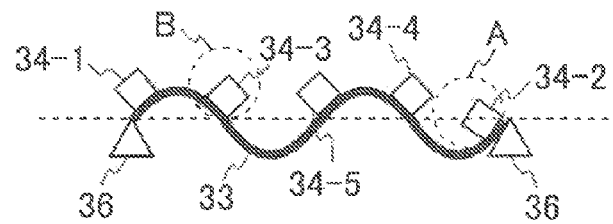
Figure 7D:
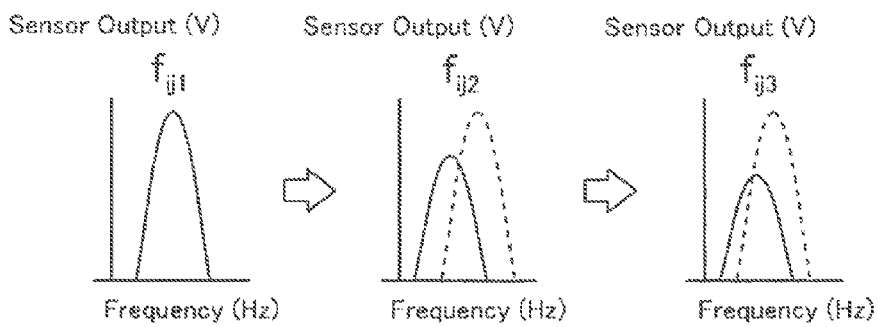
Figure 7E:
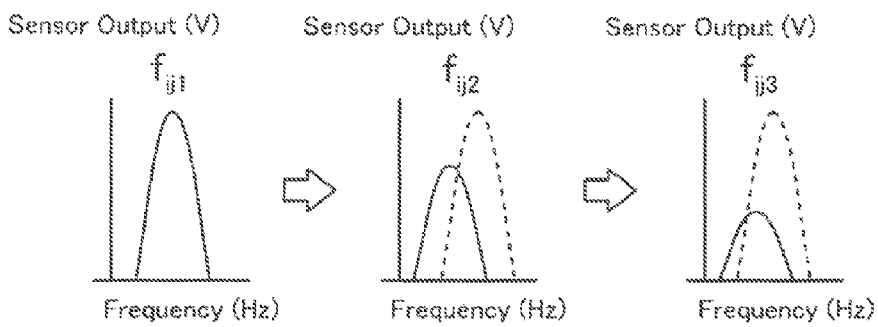

Each of FIG. 7A to FIG. 7C shows an example that a vibration sensor 34-3 is arranged just over a B part of the measurement object 33, and mechanical degradation is caused at the B part as time passes. FIG. 7A shows a frequency response at a basic resonant frequency. Each of FIG. 7B and FIG. 7C shows an example that, by adding the vibration whose frequency is swept, a high order resonant phenomenon is generated in the structure, that is, unevenness (mechanical distortion) of the vibration amplitude is caused at a plurality of points on the measurement object. FIG. 7B show a case of second order resonance, and FIG. 7C shows a case of fourth order resonance. The changes of the resonant sharpness at the vibration sensor 34-3 in these cases are shown in FIG. 7D and FIG. 7E respectively. FIG. 7D is corresponding to FIG. 7A, and FIG. 7E is corresponding to FIG. 7B. As mentioned above, in the case of adding the vibration which includes the high order resonant frequency, mechanical distortion at the degradation position B become large, and therefore a measurement value reflects the response sensitively. In this case, by comparing outputs, which are generated by plural sensors at each resonant frequency, with reference to values measured in a normal state (corresponding to standard state of the exemplary embodiment 1), the position of sensor and each resonant sharpness Q reflect the degradation point and a degree of degradation with higher level accuracy. As mentioned above, according to the present exemplary embodiment, it is possible to carry out the analysis, such as evaluation on a degree of degradation of the structure and identification of the degradation position of the structure, with higher level accuracy. While the cases of the second order resonance and the fourth order resonance have been explained in the present exemplary embodiment, the present invention is not limited to these cases. For example, a third order resonance or the like is applicable. As the high order resonant frequency, a range of the second order to the twentieth order is preferable, and a range of the second order to the tenth order is more preferable. Too high order resonant frequency tends to be difficult to be separated from a next order resonant frequency (if an order is nineteenth, next order is eighteenth or twentieth), and consequently detection becomes difficult. Therefore, it is preferable to adopt the above-mentioned range.

Exemplary Embodiment 4

Figure 8:
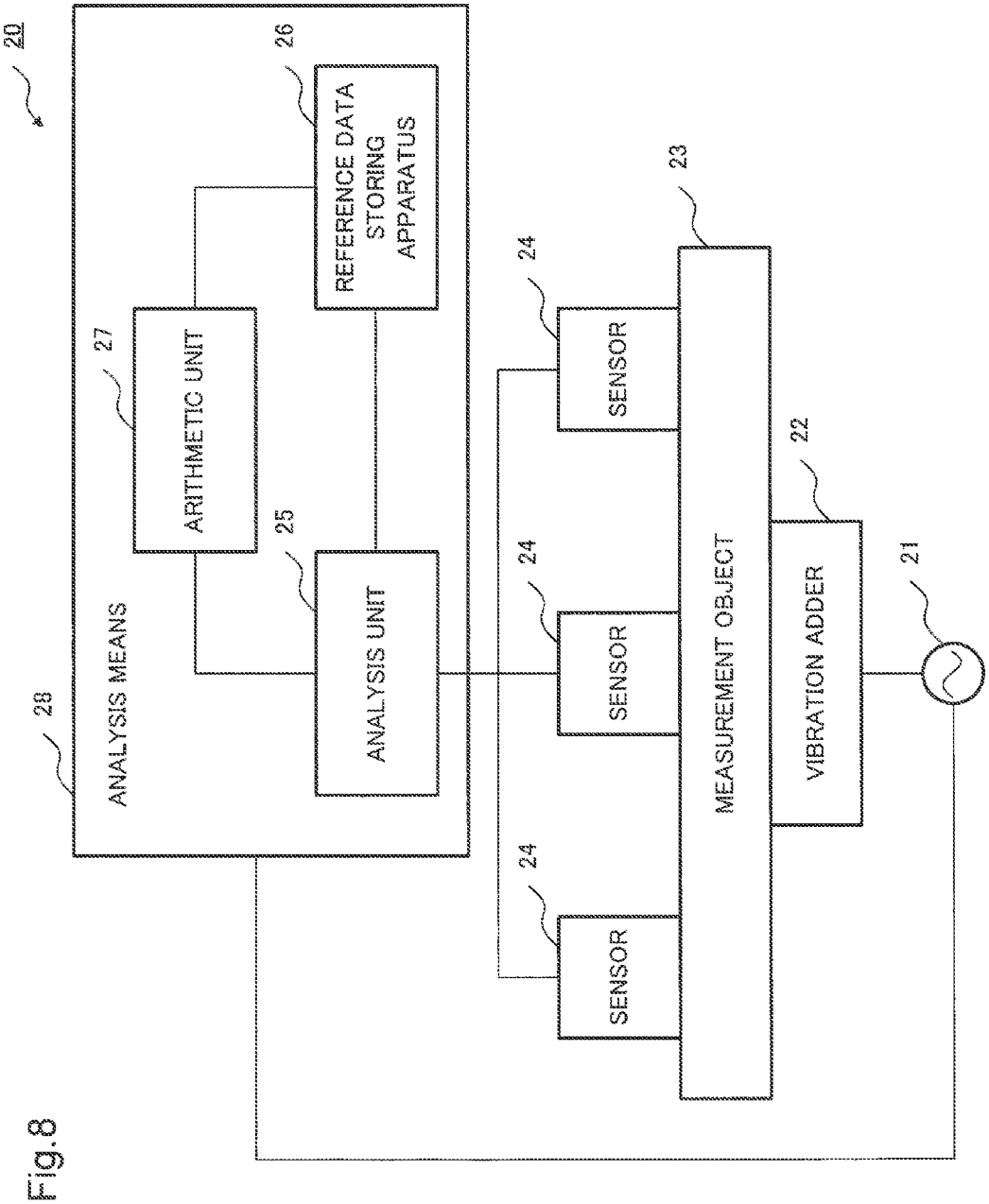
FIG. 8 is a block diagram showing composition of a structure analyzing device of an exemplary embodiment 4 of the present invention.
Figure 9A:
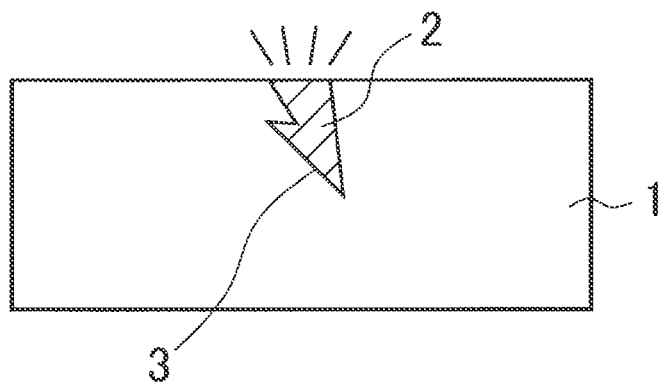
FIGS. 9A and 9B are diagrams showing an outline of a non-destructive inspection technique which is described in a non patent literature 1.
Figure 9B:
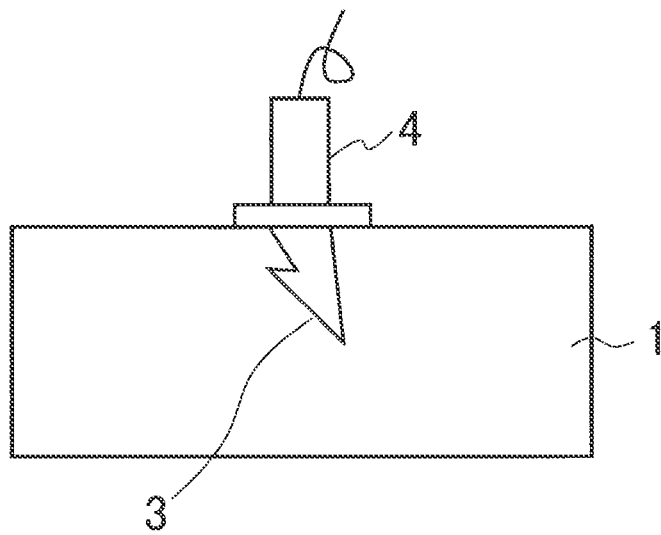

FIG. 8 is a block diagram showing composition of a structure analyzing device of an exemplary embodiment 4 of the present invention. Structure analyzing device 20 includes a constant voltage oscillation circuit 21, a vibration adder (vibration adding means) 22, a vibration acceleration sensor (vibration detecting means) 24 and an analysis means 28. The analysis means 28 includes an analysis unit 25 which calculates the resonant frequency and the resonant sharpness Q, a reference data storing apparatus 26 which stores data, and an arithmetic unit 27 which carries out comparison with reference data, and judgment. As shown in FIG. 8, structure (measurement object) 23 which is the analysis object is arranged in the structure analyzing device 20, and then analysis. As mentioned above, the vibration adder 22 may be attached to the measurement object or may not contact with the measurement object.

Exemplary Embodiment 5

The structure analyzing device and the structure analyzing method of the present invention are applicable to, for example, a leak detecting device and a leak detecting method, respectively. In the case of application to leak detection, the vibration detecting means of the structure analyzing device detects a vibration of plumbing (a water service pipe or the like, for example, a water intake pipe, a water conducting pipe, a water distributing pipe, a water supplying pipe or the like) A location where the vibration detecting means is arranged may be, for example, a manhole, a fire hydrant, a water stopping valve, a water service pipe such as a water intake pipe, a water conducting pipe, a water distributing pipe, a water supplying pipe or the like. For example, when the water conducting pipe enters into an abnormal state, and consequently an abnormal vibration and an abnormal sound are generated due to leaked water, the vibration detecting means detects the abnormal vibration, and a vibration due to the abnormal sound, and the analysis means compares a value of resonant sharpness Q, which is measured in a state existing when carrying out analysis, with a value of the resonant sharpness Q which is measured in a standard state which means that the water conducting pipe is in a non-abnormal state. As a result, it is possible to analyze a degradation state of the water conducting pipe. Similarly to the case of the water conducting pipe, it is possible to analyze a degradation state of the water service pipe other than the water conducting pipe.

Exemplary Embodiment 6

The structure analyzing device and the structure analyzing method of the present invention are applicable to, for example, an intrusion-into-building detecting device and an intrusion-into-building detecting method, respectively. In the case of application to the intrusion detection, a location where the vibration detecting means of the structure analyzing device is arranged is, for example, a window frame, glass, a door, a floor surface, a pillar or the like. By arranging the vibration detecting means on the window frame of the building, it is possible to detect an act related to intrusion, such as an act of destroying the window, unlocking the window, opening and closing the window or the like. The vibration detecting means detects a vibration due to the act related to the intrusion, and the analysis means compares a value of resonant sharpness Q, which is measured in a state existing when carrying out analysis, with a value of the resonant sharpness Q which is measured in a standard state which means a non-abnormal state. As a result, it is possible to analyze presence or absence of intrusion act.

Exemplary Embodiment 7

The structure analyzing device and the structure analyzing method of the present invention are applicable to, for example, a structure's degradation detecting device and a structure's degradation detecting method respectively. In the case of application to the structure's degradation detection, a location where the vibration detecting means of the structure analyzing device is arranged is, for example, a wall, a pillar, a beam, a floor, a foundation or the like of a building, a house or the like. For example, when the structure degrades, an abnormal vibration and an abnormal sound due to the degradation are caused. The vibration detecting means detects the abnormal vibration, and a vibration due to the abnormal sound, and the analysis means compares a value of resonant sharpness Q, which is measured in a state existing when carrying out analysis, with a value of resonant sharpness Q which is measured in a standard state meaning that the structure is in a non-abnormal state. As a result, it is possible to analyze a degradation state of the structure.

EXAMPLE

Example 1

Analysis of the structure, which has the composition shown in the block diagram of FIG. 8, was carried out by use of the structure analyzing device 20. As the analysis target structure 23, a stainless steel plate whose length, width and thickness are 40 cm, 1 cm and 5 mm respectively, was prepared. A steel ball whose weight was 1 kg was dropped repeatedly from a height of 1 m at a position, which is far from a left end of the stainless steel plate by 12 cm in a longitudinal direction of the stainless steel plate, to make the steel ball collide with the stainless steel plate. Before the steel ball was dropped, after the steel ball was dropped 1000 times, and after the steel ball was dropped 5000 times, analysis of the structure was carried out by use of the structure analyzing device 20 in a state that both ends of the stainless steel plate were supported mechanically as shown in FIG. 5B.

The vibration adder 22 was arranged at a position far from the left end of the stainless steel plate by 5 cm on the stainless steel plate, and adds a vibration, whose magnitude is 1 N, to the stainless steel plate by use of an electric signal whose frequency was swept from 10 Hz to 10 kHz. The vibration acceleration sensors 24 were arranged at four different positions far from the left side of the stainless steel plate by 4 cm, 14 cm, 24 cm and 34 cm respectively on the stainless steel plate, and voltage outputs, which were based on the positions where the sensors were arranged and which are proportional to the structure's vibration amplitude, were acquired.

Next, the basic resonant frequency and it's resonant sharpness Q are found (j=1). Furthermore, by calculating ratios of the basic resonant frequency and the resonant sharpness Q, which were acquired after the 1000 times steel ball dropping test, to the basic resonant frequency and the resonant sharpness Q respectively which were acquired before the steel ball dropping test, and calculating ratios of the basic resonant frequency and the resonant sharpness Q, which were acquired after the 5000 times steel ball dropping test, to the basic resonant frequency and the resonant sharpness Q respectively which were acquired before the steel ball dropping test, the degradation position was identified and a degree of degradation was evaluated. The result is shown in a table 1. Since it was found that, as number of the steel ball dropping tests increases, a change of the resonant sharpness Q can be recognized clearly by use of only the vibration sensor which was arranged near the position where the steel ball was dropped, it is confirmed that it was possible to identify the degradation position and to evaluate a degree of degradation with high level accuracy.

TABLE 1

| | Position 4 cm | | Position 14 cm | | Position 24 cm | | Position 34 cm | |
|---|---|---|---|---|---|---|---|---|
| | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ |
| Before steel ball dropping test | 1 | 1 | 1 | 1 | 1 | 1 | 1 | 1 |
| After 1000 times steel ball dropping tests | 1 | 1 | 0.98 | 0.92 | 1 | 1 | 1 | 1 |
| After 5000 times steel ball dropping tests | 1 | 1 | 0.88 | 0.80 | 1 | 1 | 1 | 1 |

Example 2

Similarly to the example 1, the test of dropping the steel ball against the stainless steel plate was carried out. In this case, the resonant sharpness Q related to a secondly low resonant frequency from the basic resonant frequency (second order resonant frequency: j=2) was used for identifying a degradation position and evaluating a degree of degradation. The result is shown in a table 2. A change of an output value of the sensor, which was arranged near to the position where the steel ball was dropped, was observed similarly to the example 1, and the change of the output value was large in comparison with the change according to the example 1. It was conceivable that the measurement reflected a degree of degradation sensitively since the large mechanical distortion was caused at the high order resonant frequency which is generated by the frequency sweeping. It was confirmed that an accurate measurement was carried out by using the high order resonant frequency as mentioned above.

TABLE 2

| | Position 4 cm | | Position 14 cm | | Position 24 cm | | Position 34 cm | |
|---|---|---|---|---|---|---|---|---|
| | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ |
| Before steel ball dropping test | 1 | 1 | 1 | 1 | 1 | 1 | 1 | 1 |
| After 1000 times steel ball dropping tests | 1 | 1 | 0.85 | 0.80 | 1 | 1 | 1 | 1 |
| After 5000 times steel ball dropping tests | 1 | 1 | 0.65 | 0.55 | 1 | 1 | 1 | 1 |

Example 3

Similarly to the example 1, the test of dropping the steel ball against the stainless steel plate was carried out. In this case, the resonant sharpness Q related to a thirdly low resonant frequency from the basic resonant frequency (third order resonant frequency: j=3) was used for identifying a degradation position and evaluating a degree of degradation. The result is shown in a table 3. The change of the output value of the sensor, which was arranged at the position where the steel ball was dropped, was observed similarly to the example 1 and the example 2, and the change of the output value was large in comparison with the changes according to the example 1 and the example 2. It was conceivable that the measurement reflected a degree of degradation more sensitively since the large mechanical distortion was caused at the high order resonant frequency. It was confirmed that the more accurate measurement was carried out by use of the higher order resonant frequency as mentioned above.

TABLE 3

|  | Position 4 cm | | Position 14 cm | | Position 24 cm | | Position 34 cm | |
| --- | --- | --- | --- | --- | --- | --- | --- | --- |
|  | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ |
| Before steel ball dropping test | 1 | 1 | 1 | 1 | 1 | 1 | 1 | 1 |
| After 1000 times steel ball dropping tests | 1 | 1 | 0.70 | 0.75 | 1 | 1 | 1 | 1 |
| After 5000 times steel ball dropping tests | 1 | 1 | 0.35 | 0.30 | 1 | 1 | 1 | 1 |

Example 4

Similarly to the example 3 except for using a laser Doppler vibrometer in place of the vibration acceleration sensor, the test of dropping the steel ball against the stainless steel plate was carried out. The result is shown in a table 4. Since the same result as the result in the example 3 was acquired also in the example, it was found that the result does not depend on a kind of the sensor, which detects the vibration amplitude, in the present invention.

TABLE 4

|  | Position 4 cm | | Position 14 cm | | Position 24 cm | | Position 34 cm | |
| --- | --- | --- | --- | --- | --- | --- | --- | --- |
|  | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ |
| Before steel ball dropping test | 1 | 1 | 1 | 1 | 1 | 1 | 1 | 1 |
| After 1000 times steel ball dropping tests | 1 | 1 | 0.69 | 0.74 | 1 | 1 | 1 | 1 |
| After 5000 times steel ball dropping tests | 1 | 1 | 0.34 | 0.31 | 1 | 1 | 1 | 1 |

Example 5

Similarly to the example 3 except for adding the vibration to the structure by use of sound waves emitted by a speaker in place of the vibration adder, the test of dropping the steel ball against the stainless steel plate was carried out. The result is shown in a table 5. Since the same result as the result in the example 3 was acquired also in the example, it was found out that the analysis result was acquired independently of the vibration adding method in the present invention.

TABLE 5

|  | Position 4 cm | | Position 14 cm | | Position 24 cm | | Position 34 cm | |
| --- | --- | --- | --- | --- | --- | --- | --- | --- |
|  | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ | $f_{ijk}/f_{ijl}$ | $Q_{ijk}/Q_{ijl}$ |
| Before steel ball dropping test | 1 | 1 | 1 | 1 | 1 | 1 | 1 | 1 |
| After 1000 times steel ball dropping tests | 1 | 1 | 0.70 | 0.75 | 1 | 1 | 1 | 1 |
| After 5000 times steel ball dropping tests | 1 | 1 | 0.35 | 0.30 | 1 | 1 | 1 | 1 |

Example 6

In the present example, a simulation on a case that physical properties of a whole of the stainless steel plate, which was the same as the stainless steel plate used in the example 1 (length, width, and thickness are 40 cm, 1 cm and 5 mm, respectively), are changed was carried out. The result is shown in a table 6. In the table 6, fr is the resonant frequency (normalized value whose reference is a value measured before degradation), and Q is the resonant sharpness (normalized value whose reference is a value measured before degradation). On the assumption that the Young's modulus and the attenuation coefficient of the stainless steel plate before degradation were 1 and 1 respectively, and the Young's modulus after the degradation and the attenuation coefficient after the degradation are 0.98 and 1.06 respectively, the simulation was carried out by use of the finite element method.

TABLE 6

| state | before degradation | after degradation |
| --- | --- | --- |
| fr | 1 | 0.99 |
| Q | 1 | 0.94 |

As shown in the table 6, a difference between the resonant frequency fr before the degradation, and the resonant frequency fr after the degradation is 1%, and a difference between the resonant sharpness Q before the degradation, and the resonant sharpness Q after the degradation is 6%. It is conceivable that, even in the case that it is difficult to detect the degradation on the basis of the change of the resonant frequency since a change of the physical properties of the material is slight as mentioned above, it is possible to detect the degradation by comparing the value of the resonant sharpness Q, which is measured in the state existing when carrying out the analysis, with the value of the resonant sharpness Q which is measured in the standard state since the change of the resonant sharpness Q is large.

While the invention has been particularly shown and described with reference to exemplary embodiments and examples thereof, the invention is not limited to these embodiments and examples. It will be understood by those of ordinary skill in the art that various changes in form and details may be made therein without departing from the spirit and scope of the present invention as defined by the claims.

This application is based upon and claims the benefit of priority from Japanese Patent Application No. 2012-129199, filed on Jun. 6, 2012, the disclosure of which is incorporated herein in its entirety by reference.

INDUSTRIAL APPLICABILITY

The structure analyzing device and the structure analyzing method of the present invention are applicable to a structure made of stainless steel, aluminum alloy and concrete, and a vinyl chloride pipe. For example, the structure analyzing device and the structure analyzing method according to the present invention are applicable to detecting water leak or destruction of a water service pipe in a water service system of a social infrastructure business, detecting degradation of a structure such as a building or a house, detecting petroleum leak or destruction of a pipeline in a petroleum pipe line system, and detecting gas leak in a gas pipeline or destruction of the pipeline. Use of the invention has no limitation and has wide scope.

REFERENCE SIGNS LIST 10 and 20 structure analyzing device
11 vibration detecting means
12 analysis means
13 vibration adding means
14 control means
21 constant voltage oscillation circuit
22 and 32 vibration adder
23 structure of analysis object (measurement object)
24 vibration acceleration sensor
25 analysis unit
26 reference data storing apparatus
27 arithmetic unit
28 analysis means
33 measurement object
34-1 to 34-5 vibration sensor
36 pedestal
1 member
2 fluorescent material
3 crack
4 ultrasonic transducer

The invention claimed is:

1. A structure analyzing device, comprising:
a plurality of vibration detecting sensors configured to detect a vibration of a structure; and
a processor configured to analyze an output signal of the plurality of vibration detecting sensors, wherein
the plurality of vibration detecting sensors are arranged respectively at locations different from each other in the structure,
the processor analyzes distribution of change in the structure by comparing a measured value of a resonant sharpness Q, which is calculated by use of the following formula (1), with a standard value of the resonant sharpness Q, and comparing the measured value of the resonant sharpness Q of each sensor in high order resonant frequency, $$Q = f/\Delta f \tag{1}$$

where f is a resonant frequency of the structure, and $\Delta f$ is a full width at half maximum, and
the processor identifies a degradation position of the structure based on a result of a comparison with respect to the resonant sharpness Q of each sensor in the high order resonant frequency.

2. The structure analyzing device according to claim 1, wherein the standard value of the resonant sharpness Q is a value in a state before the change occurs in the structure.

3. The structure analyzing device according to claim 1, wherein the standard value of the resonant sharpness Q is stored in a storage device, and wherein
the processor reads the standard value of the resonant sharpness Q from the storage device, and compares the measured value of the resonant sharpness Q with the standard value of the resonant sharpness Q.

4. The structure analyzing device according to claim 1, wherein the plurality of vibration detecting sensors are contact sensors.

5. The structure analyzing device according to claim 1, further comprising:
a vibration adding device which vibrates the structure.

6. The structure analyzing device according to claim 5, wherein
the vibration adding device adds a vibration, which includes a high order resonant frequency component, to the structure, and causes the structure mechanical distortion, and wherein
at least one of the plurality of vibration detecting sensors is arranged at a position at which the mechanical distortion is caused.

7. A non-destructive inspection apparatus, comprising:
the structure analyzing device according to claim 1.

8. A leak analyzing device, comprising:
the structure analyzing device according to claim 1, wherein
the plurality of vibration detecting sensors detect a vibration of plumbing, and
the processor analyzes a degradation state of the plumbing by comparing a value of the resonant sharpness Q of the plumbing.

9. A structure analyzing method, comprising:
detecting a vibration of a structure; and
analyzing an output signal being output, wherein
analyzing a state change of the structure, by comparing a measured value of a resonant sharpness Q, which is calculated by use of the following formula (1), with a standard value of the resonant sharpness Q, and comparing the measured value of the resonant sharpness Q of each sensor in high order resonant frequency, $$Q = f/\Delta f \tag{1}$$

where f is a resonant frequency of the structure, and $\Delta f$ is a full width at half maximum, and identifying a degradation position of the structure based on a result of a comparison with respect to the resonant sharpness Q of each sensor in the high order resonant frequency.

10. The structure analyzing method according to claim 9, wherein the standard value of the resonant sharpness Q is a value in a state before the change occurs in the structure.

11. The structure analyzing method according to claim 9, wherein the standard value of the resonant sharpness Q is stored, and wherein reading the standard value of the resonant sharpness Q and comparing the measured value of the resonant sharpness Q.

12. The structure analyzing method according to claim 9, further comprising:

vibrating a structure, before detecting a vibration of a structure.

13. The structure analyzing method according to claim 12, further comprising:

adding a vibration including a high order resonant frequency component of the structure, and in which by adding the vibration, cause the mechanical distortion to the structure, detecting a vibration of the structure caused at a position, at which the mechanical distortion is caused, and analyzing a state change of the structure on the basis of an output signal related to the vibration of the structure existing at the position at which the mechanical distortion is caused.

14. A non-destructive inspection method which uses the structure analyzing method according to claim 9.

15. A leak analyzing method which uses the structure analyzing method according to claim 9, wherein detecting a vibration of plumbing is detected, and wherein analyzing, a degradation state of the plumbing, by comparing the value of resonant sharpness Q of the plumbing.

* * * * *